(12) United States Patent
Frisch et al.

(10) Patent No.: US 7,647,090 B1
(45) Date of Patent: Jan. 12, 2010

(54) IN-VIVO SENSING DEVICE AND METHOD FOR PRODUCING SAME

(75) Inventors: Mordechai Frisch, Moreshet (IL); Arkady Glukhovsky, Santa Clarita, CA (US)

(73) Assignee: Given Imaging, Ltd., Yoqneam (IL)

( * ) Notice: Subject to any disclaimer, the term of this patent is extended or adjusted under 35 U.S.C. 154(b) by 477 days.

(21) Appl. No.: 11/024,906

(22) Filed: Dec. 30, 2004

Related U.S. Application Data

(60) Provisional application No. 60/532,914, filed on Dec. 30, 2003.

(51) Int. Cl.
*A61B 6/00* (2006.01)
*A61B 1/04* (2006.01)
*A61B 1/06* (2006.01)

(52) U.S. Cl. .................. 600/473; 600/109; 600/160; 600/476

(58) Field of Classification Search ............... 600/437, 600/473; 348/77; 128/903
See application file for complete search history.

(56) References Cited

U.S. PATENT DOCUMENTS

| | | | |
|---|---|---|---|
| 3,971,362 A | 7/1976 | Pope et al. | |
| 4,239,040 A | 12/1980 | Hosoya et al. | |
| 4,278,077 A | 7/1981 | Mizumoto | |
| 4,439,197 A | 3/1984 | Honda et al. | |
| 4,646,724 A | 3/1987 | Sato et al. | |
| 4,689,621 A | 8/1987 | Kleinberg | |
| 4,803,992 A | 2/1989 | Lemelson | |
| 4,819,620 A | 4/1989 | Okutsu | |
| 4,844,076 A | 7/1989 | Lesho et al. | |
| 4,936,823 A | 6/1990 | Colvin et al. | |
| 5,187,572 A | 2/1993 | Nakamura et al. | |
| 5,267,033 A | 11/1993 | Hoshino | |
| 5,279,607 A | 1/1994 | Schentag et al. | |
| 5,330,427 A | 7/1994 | Weissenburger | |
| 5,368,027 A | 11/1994 | Lubbers et al. | |
| 5,395,366 A * | 3/1995 | D'Andrea et al. | 604/890.1 |
| 5,398,670 A | 3/1995 | Ortiz et al. | |
| 5,495,114 A | 2/1996 | Adair | |
| 5,558,640 A | 9/1996 | Pfeiler et al. | |
| 5,604,531 A | 2/1997 | Iddan et al. | |
| 5,697,384 A | 12/1997 | Miyawaki et al. | |
| 5,819,736 A | 10/1998 | Avny et al. | |
| 5,929,901 A | 7/1999 | Adair et al. | |

(Continued)

FOREIGN PATENT DOCUMENTS

DE     34 40 177     6/1986

(Continued)

OTHER PUBLICATIONS

U.S. Appl. No. 09/807,892, filed Jun. 6, 2001, Meron et al.

(Continued)

*Primary Examiner*—Eric F Winakur
*Assistant Examiner*—Katherine L Fernandez
(74) *Attorney, Agent, or Firm*—Pearl Cohen Zedek Latzer, LLP

(57) ABSTRACT

An in-vivo sensing device may include, for example, an in-vivo sensing module attached to a functional module. The in-vivo sensing module may include, for example, an in-vivo imager or sensor. The functional module may include, for example, a power source, a transmitter, or other components.

20 Claims, 9 Drawing Sheets

U.S. PATENT DOCUMENTS

| | | | |
|---|---|---|---|
| 5,986,693 | A | 11/1999 | Adair et al. |
| 5,993,378 | A | 11/1999 | Lemelson |
| 6,043,839 | A | 3/2000 | Adair et al. |
| 6,099,482 | A | 8/2000 | Brune et al. |
| 6,149,581 | A | 11/2000 | Klingenstein |
| 6,233,476 | B1 | 5/2001 | Strommer et al. |
| 6,240,312 | B1 * | 5/2001 | Alfano et al. .............. 600/476 |
| 6,692,430 | B2 | 2/2004 | Adler |
| 2001/0035902 | A1 | 11/2001 | Iddan et al. |
| 2002/0103417 | A1 | 8/2002 | Gazdzinski |
| 2002/0146368 | A1 | 10/2002 | Meron et al. |
| 2002/0158976 | A1 | 10/2002 | Vni et al. |
| 2002/0177779 | A1 | 11/2002 | Adler et al. |
| 2003/0018280 | A1 * | 1/2003 | Lewkowicz et al. ......... 600/549 |
| 2003/0028078 | A1 | 2/2003 | Glukhovsky |
| 2003/0045790 | A1 | 3/2003 | Lewkowicz et al. |
| 2003/0114742 | A1 | 6/2003 | Lewkowicz et al. |
| 2003/0167000 | A1 | 9/2003 | Mullick et al. |
| 2003/0195415 | A1 | 10/2003 | Iddan |
| 2003/0208107 | A1 | 11/2003 | Refael |
| 2003/0214579 | A1 | 11/2003 | Iddan |
| 2003/0214580 | A1 | 11/2003 | Iddan |
| 2003/0216622 | A1 | 11/2003 | Meron et al. |

FOREIGN PATENT DOCUMENTS

| | | |
|---|---|---|
| FR | 2 688 997 | 10/1993 |
| IL | 143259 | 5/2001 |
| JP | 4144533 | 5/1992 |
| JP | 6114037 | 4/1994 |
| JP | 6285044 | 10/1994 |
| JP | 7111985 | 5/1995 |
| JP | 2000342522 | 12/2000 |
| JP | 2001091860 | 4/2001 |
| JP | 2001095755 | 4/2001 |
| JP | 2001095756 | 4/2001 |
| JP | 2001104241 | 4/2001 |
| JP | 2001104242 | 4/2001 |
| JP | 2001104243 | 4/2001 |
| JP | 2001104244 | 4/2001 |
| JP | 2001104287 | 4/2001 |
| JP | 2001112709 | 4/2001 |
| JP | 2001112710 | 4/2001 |
| JP | 2001112740 | 4/2001 |
| JP | 2001137182 | 5/2001 |
| JP | 2001231744 | 8/2001 |
| JP | 2001245844 | 9/2001 |
| JP | 2000342524 | 6/2002 |
| JP | 2000342525 | 6/2002 |
| WO | WO 00/22975 | * 4/2000 |
| WO | WO 01/50941 | 7/2001 |
| WO | WO 01/69212 | 9/2001 |
| WO | WO 02/055126 | 7/2002 |
| WO | WO 02/094337 | 11/2002 |
| WO | WO 03/003706 | 1/2003 |
| WO | WO 03/011103 | 2/2003 |
| WO | WO 2004/028336 | 4/2004 |
| WO | WO 2004/035106 | 4/2004 |

OTHER PUBLICATIONS

U.S. Appl. No. 10/200,548, filed Jul. 23, 2002, Glukhovsky et al.
U.S. Appl. No. 10/724,109, filed Dec. 1, 2003, Glukhovsky et al.
U.S. Appl. No. 10/166,025, filed Jun. 11, 2002, Lewkowicz et al.
U.S. Appl. No. 10/213,345, filed Aug. 7, 2002, Glukhovsky.
"The Heidelburg pH Capsule System Telemetric Fasting Gastric Analysis", Heidelburg International. Incorporated.
Heidelberger Kapsel—ein Kleinstsender fur die pH-Messung im Magen, Lange, et al., Telefunken-Zeitung, Jg 36 (1963) Heft 5, pp. 265-270.
"New Smart Plastic has Good Memory"—Turke, European Medical Device Manufacturer, devicelink.com.
"Robots for the Future"—Shin-ichi, et al. http://jin.jcic.or.jp/nipponaia13/sp05 html. printed Nov. 29, 2001.
"The Radio Pill", Rowlands, et al., British Communications and Electronics, Aug. 1960, pp. 598-601.
Video Camera to "TAKE"—RF System Lab, Dec. 25, 2001.
"Wellesley Company Sends Body Montiors into Space"—Crum, Boston Business Journal, 1998.
www.rfnorkia.com—NORIKA3, printed on Jan. 1, 2002.
"Wireless Transmission of a Color Television Moving Image from the Stomach using a Miniature CCD Camera, Light Source and Microwave Transmitter." Swain CP, Gong F, Mills TN. Gastrointest Endosc 1997;45:AB40, vol. 45, No. 4, 1997.
"In Pursuit of the Ultimate Lamp", Craford et al., Scientific American, Feb. 2001.
Manual of Photogrammetry, Thompson (Ed.), Third Edition, vol. Two, Copyright 1944, 1952, 1966 by the American Society of Photogrammetry.
www.jason.net/tinycam.htm, © 2001, printed Dec. 19, 2001.
www.middleeasthealthmag.com/article2.htm—Review proves the value of computers, © 2001, printed Nov. 29, 2001.
www.pedinc.com Personal electronic devices, © 1997.
BBC News Online—Pill camera to 'broadcast from the gut', Feb. 21, 2000, www.news.bbc.co.uk, printed Oct. 22, 2002.

* cited by examiner

IN-VIVO SENSING DEVICE AND METHOD FOR PRODUCING SAME

PRIOR APPLICATION DATA

This application claims benefit and priority from U.S. Provisional Patent Application No. 60/532,914, entitled "In Vivo Sensing Module with Attachable Functional Module", filed on Dec. 30, 2003, which is incorporated herein by reference in its entirety.

FIELD OF THE INVENTION

The present invention relates to devices, system and methods of in-vivo sensing and in-vivo imaging.

BACKGROUND OF THE INVENTION

Some in-vivo imaging devices may include an in-vivo measurement system, for example, an in-vivo video camera system. In an ingestible in-vivo imaging device, the in-vivo camera system may capture and transmits images of, for example, the gastro-intestinal (GI) tract while the in-vivo device passes through the GI lumen. An in-vivo imaging system may include, for example, a swallowable capsule able to pass through the entire digestive tract and able to operate as an autonomous video endoscope.

Other devices, systems and methods for in-vivo sensing of passages or cavities within a body, and for sensing and gathering information (e.g., image information, pH information, temperature information, electrical impedance information, pressure information, etc.), are known in the art.

There may be a need for a plurality of uses for in-vivo sensing devices, each of which may require a different arrangement of elements within the device. Manufacturing multiple in-vivo devices for different uses may be expensive.

SUMMARY OF THE INVENTION

According to some embodiments of the present invention, an in-vivo sensing module, for example, an in-vivo imaging module, may be attached or detachably attached to various functional modules. Thus, for example, manufacturing of multiple devices to achieve various functionalities may not be necessary or may be more efficient.

Embodiments of the invention may allow various other benefits, and may be used in conjunction with various other applications.

BRIEF DESCRIPTION OF THE DRAWINGS

The present invention will be understood and appreciated more fully from the following detailed description taken in conjunction with the drawings in which.

Figure 1:
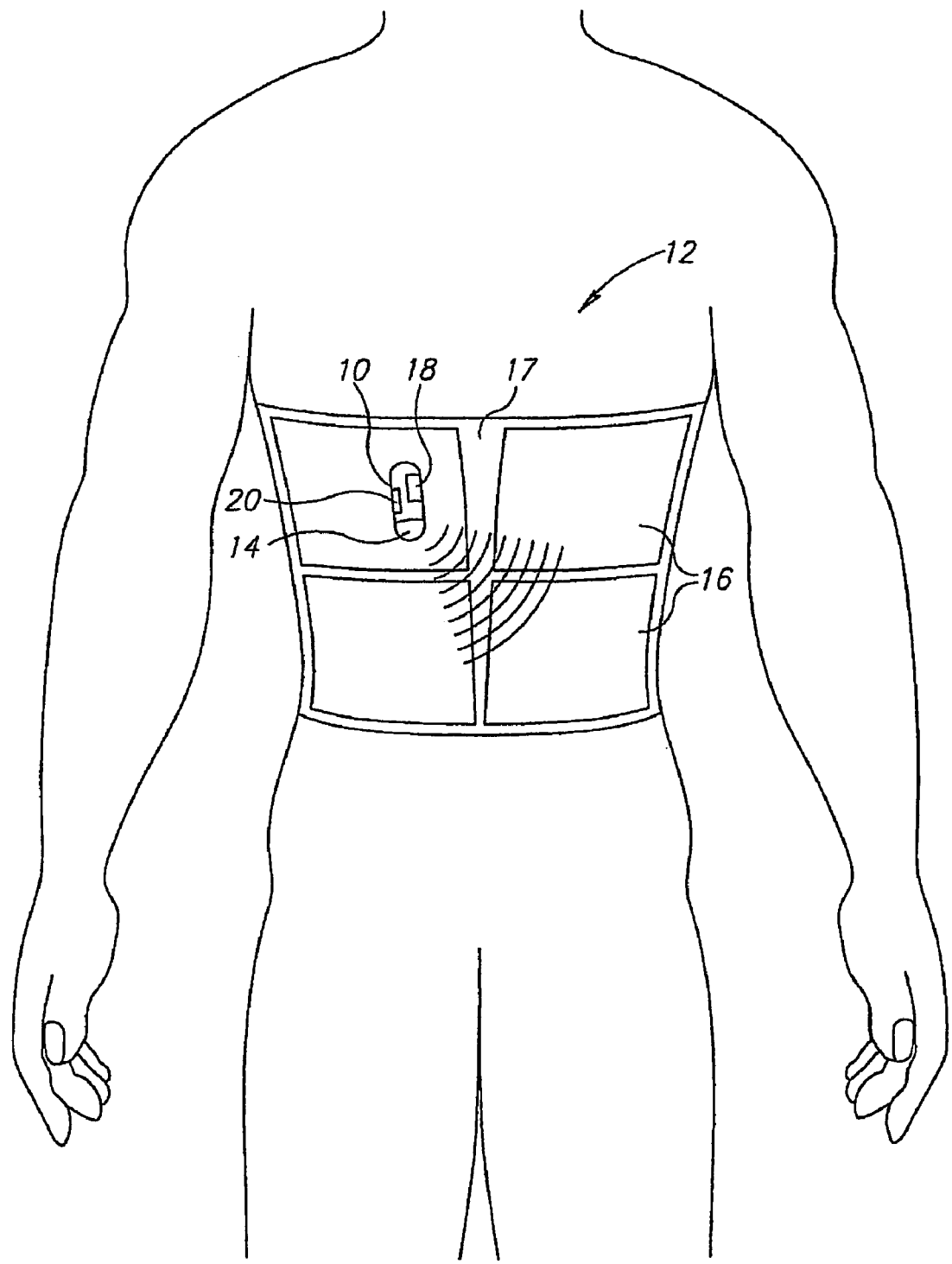
FIG. 1 is a schematic illustration of an ingestible in-vivo sensing device.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

While a portion of the discussion may relate, for exemplary purposes, to features, functionalities and components of an in-vivo sensing or imaging device, the present invention is not limited in this regard, and may be used not necessarily in the context of in-vivo sensing or imaging.

The device, system and method of the present invention may be used with or in an imaging system, and a receiving, recording and display system such as that described in International Publication Number WO 01/65995, entitled "A Device and System for In-Vivo Imaging", international publication date Sep. 13, 2001, international filing date Mar. 8, 2001. A further example of an imaging system, and a receiving, recording and display system with which or in which the device, system and method of the present invention may be used, is described in U.S. Pat. No. 5,604,531 to Iddan et al., entitled "In-Vivo Video Camera System", filed on Jan. 17, 1995. Both these publications are assigned to the common assignee of the present application and are hereby incorporated by reference. The device, system and method of the present invention may be utilized in conjunction with other suitable devices, systems and methods providing images of a body lumen or cavity or performing other in-vivo sensing operations.

Some devices and systems as described herein may have other configurations and/or other sets of components. For example, some embodiments of the present invention may be practiced using an endoscope, needle, stent, probe, catheter, etc.

FIG. 1 shows an in-vivo sensing device 10, for example, an ingestible or swallowable capsule, within a body 12. Device 10 may include, for example, an imaging unit 14, e.g., located at one end of device 10. Once swallowed or otherwise inserted into body 12, the imaging unit 14 may acquire and transmit images of, for example, the gastro-intestinal (GI) tract, e.g., to one or more antennas 16 within an antenna belt 17 or other receiving system possibly surrounding a portion of body 12. Device 10 may include a power source, e.g., one or more batteries 18 able to provide power to the various components of device 10. In some embodiments, device 10 may also include functional elements 20, which may provide non-imaging functionalities to device 10. For example, functional elements 20 may include a non-imaging sensor such as a temperature or pH sensor, a blood tester, or other suitable components.

Figure 2:
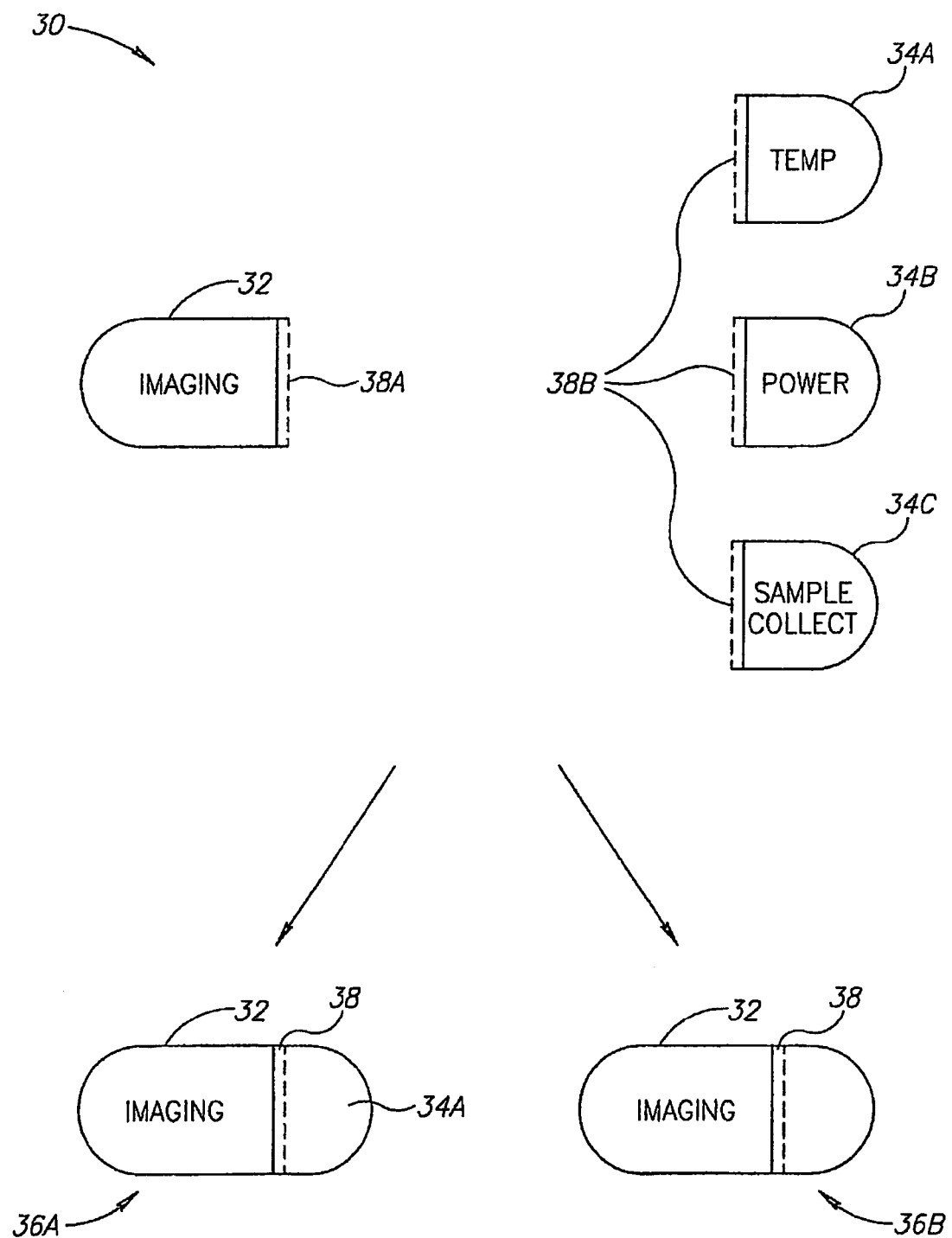
FIG. 2 is a schematic illustration of an in vivo sensing device assembled and operative according to some embodiments of the invention.

FIG. 2 schematically illustrates a multi-part sensing system 30 in accordance with some embodiments of the present invention. According to one embodiment, system 30 may include a sensing module, such as imaging module 32, and one or more functional modules, for example, functional modules 34A, 34B and 34C. Although three functional modules 34A-34C are shown, other suitable numbers of functional modules may be used. Functional modules and sensing modules, or their components, may be interchanged; for example, various possible functional modules may be attached to or included in a sensing module, and a standard interface or connections system can be used to connect the modules.

System 30 may be used to produce a multiplicity of in-vivo sensing devices or in-vivo imaging devices, for example, devices 36A and 36B (which may be or may include, for example, a swallowable capsule), each device formed of an imaging module 32 to which at least one functional module 34 may be attached, or detachably attached. For example, device 36A may be formed from imaging module 32 and a temperature sensing module 34A, and device 36B may be formed from imaging module 32 and a sample collecting unit 36C. Embodiments of the invention may include other in-vivo sensing devices having a first member attached to a second member, wherein the first member may include, for example, an in-vivo imaging unit or a unit having an in-vivo sensing capability. In accordance with some embodiments of the invention, such modules or members may be configured, shaped, or formed to adaptively connect or attach to other modules or members, e.g., using a suitable attachment mechanism as described herein.

According to some embodiments, imaging module 32 may include, but need not include, imaging capabilities; for example, imaging module 32 may include signal transmitting capabilities, e.g., a transmitter. According to some embodiments, the components of system 30 may be, but need not be, capsule shaped, or may have a shape of at least a portion of a capsule; other suitable shapes for in-vivo sensing or imaging devices may be used. According to some embodiments, the various modules (e.g., imaging modules, sensing modules, functional modules, or the like), when interconnected, assembled or attached, may be, but need not be, capsule shaped; other suitable shapes for in-vivo sensing or imaging devices may be used In some embodiments, and as described in detail herein (for example, with regard to FIG. 3), imaging module 32 may include one or more elements for imaging a body lumen within which system 30 may be, and/or for transmitting image data or other data from the system 30 to an external receiver. Functional modules 34 may be attached to imaging module 32 at any suitable time, for example, during manufacture or prior to an operation or a process requiring a specific type of in-vivo device. For example, before administering an in-vivo device to a patient, a health professional may attach or connect a suitable functional module selected from a set of modules, to an imaging module or a sensing module, or may otherwise assemble an in-vivo imaging or sensing device from a set of such modules. Multiple attachment mechanisms 38 (e.g., as shown as dotted lines in FIG. 2) may be used, and may utilize a portion 38A on imaging module 32 and a portion 38B on the functional modules 34. Some exemplary attachment systems are shown herein with regard to FIGS. 4, 5A, 5B, 6 and 7.

In some embodiments, each functional module 34 may perform one or more functions. The functions may include any suitable function that may be performed within a body lumen, such as, for example, sensing in-vivo parameters, e.g., temperature, pressure, and/or pH (e.g., module 34A), sample collecting (e.g., sample collecting module 34C), biopsy collecting, micro-surgery, drug delivery, ultrasound sensing, bio-detecting, or the like. In some embodiments, functional module 34 may also affect the movement of device 36, for example, by providing additional propulsion using an acceleration mechanism, by providing a breaking or decelerating mechanism to temporarily stop or slow-down the motion of device 36, or by otherwise modifying a movement or a movement parameter (e.g., velocity, acceleration, deceleration, orientation, direction, or the like) of device 36. In some embodiments, functional module 34B may provide additional energy or electrical power. Any suitable function which may be added to the sensing operation of imaging module 32 may be placed into a functional module 34.

Figure 3:
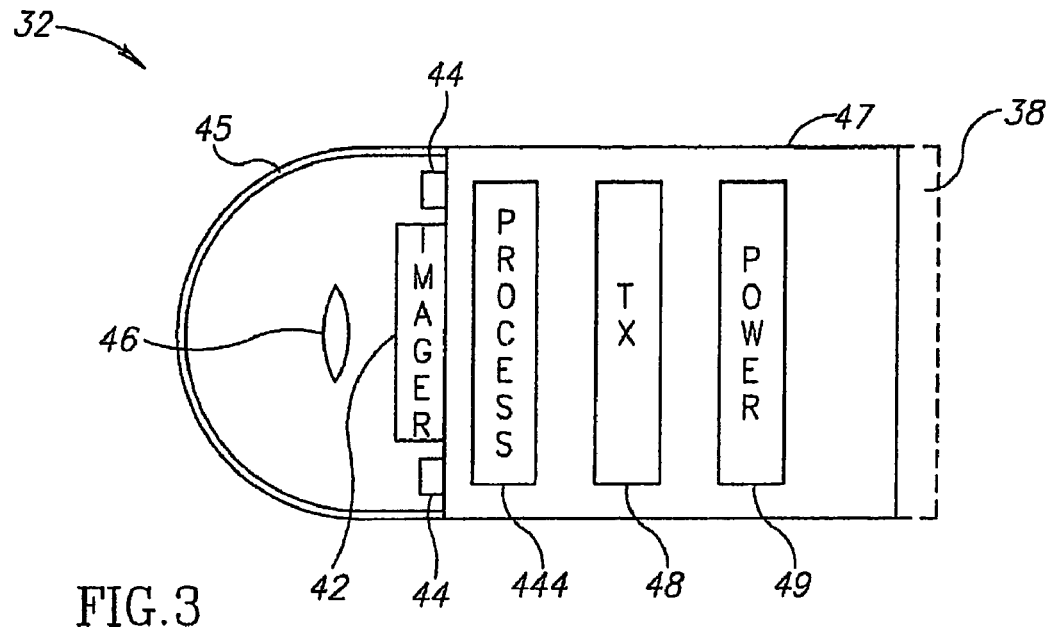
FIG. 3 is a schematic illustration of an in-vivo imaging module according to an embodiment of the invention.

Reference is now made to FIG. 3, which illustrates an exemplary imaging module 32 in accordance with some embodiments of the invention. Embodiments of the imaging module may include components and/or may operate similarly to embodiments described in an imaging system such as that described in International Publication Number WO 01/65995, entitled "A Device and System for In-Vivo Imaging", international publication date Sep. 13, 2001, international filing date Mar. 8, 2001, and/or as described in U.S. Pat. No. 5,604,531 to Iddan et al., entitled "In-Vivo Video Camera System", filed on Jan. 17, 1995, both assigned to the common assignee of the present application and hereby incorporated by reference; however, the present invention may be used with other sensing systems or other arrangements of components.

Embodiments of the invention may include a typically autonomous in-vivo sensing device, e.g., which may progress through a body lumen independently of external manipulation and not requiring a wired connection to an external source. Some embodiments may include, for example, immoblizable sensing devices, wherein a device may be immobilized to a body lumen wall for monitoring a certain in-vivo location over an extended period of time.

According to some embodiments, imaging module 32 may include an image sensor 42, such as a CCD or CMOS imager, one or more illumination source(s) 44, e.g., a Light Emitting Diode (LED), a window 45 and an optical system 46, shown schematically as a lens, typically for focusing light or images onto the image sensor 42. Imaging module 32 may further include a transmitter 48 and a power source 49, e.g., one or more battery units.

Transmitter 48 may, for example, operate wirelessly via radio waves, and may optionally be connected to an antenna, for transmitting images and possibly other information to, for example, a receiving device. Other types of transmitters may be used.

In some embodiments, transmitter 48 includes control capability for, for example controlling the various operations of the in-vivo device, although control capability or one or more aspects of control may be included in a separate component. Transmitter 48 is typically an Application Specific Integrated Circuit (ASIC), but may be of other constructions; for example, transmitter 48 may be or may include a processor able to execute instructions. The in-vivo device may include a processing unit separate from transmitter 48 that may, for example, contain or process instructions.

Optionally, a processing unit 444 may carry out certain conditioning, processing or modification of the image data or image signal, for example, so that it may be viewed on a display system such as on a monitor. An example of a processor chip that may be used in embodiments of the present invention is an Application Specific Integrated Circuit (ASIC). According to one embodiment, the ASIC may have transmitting capabilities, for example, operating on a Minimum Shift Keying (MSK) modulation system to effect transmitting of digital signals through an antenna through radio frequencies to a receiving system. The ASIC may also control the illumination and imager, for example as described in the above-mentioned WO 01/65995. In alternate embodiments, other signals and other electronic and processing components may be used.

Processing unit 444 may, for example, contain and/or process instructions. In some embodiments for examples, instructions embodying an error correction code, an image analysis code, an image modification code, a data compression code, or other suitable instructions, may be included in an optional memory unit that may be part of or connected to processing unit 444. Processing unit 444 or its functionality may be included in transmitter 48; in alternate embodiments such functionality may be placed in other units.

In some embodiments, window 45 may have a partially spherical shape and may attach to a cylindrical housing 47, which may enclose at least transmitter 48 and power source 49. Housing 47 may further include attachment mechanism 38. Transmitter 48 may transmit image data and/or other (e.g., non-image) information to a receiving device, and may include other components, such as, for example, a compression module for compressing data, a receiver module, a transceiver module, or the like. According to an embodiment of the invention, transmitter 48 may include an ultra low power Radio Frequency (RF) transmitter having high bandwidth input, possibly provided in chip scale packaging. The transmitter 48 may further include circuitry and functionality for controlling the in-vivo device. The transmitter 48 may be or may include, for example, an ASIC, a "computer on a chip", a microcontroller, or other suitable components.

In some embodiments, components such as the image sensor 42, illumination source(s) 44 and transmitter 48 may optionally be mounted on a support, which may include, for example, a printed circuit board or plastic board or sheet. The support may be another structure, and components need not be mounted on a separate support. Other components may be included in imaging module 32. Power source 49 may be any suitable battery or batteries capable of powering at least image sensor 42, illumination source(s) 44, and transmitter 48 during the time imaging module 32 may be within the body lumen.

Reference is now made to FIGS. 4, 5A, 5B, 6 and 7, which illustrate some exemplary attachment and electrical contact mechanisms, constructed and operative in accordance with some embodiments of the invention.

Figure 4:
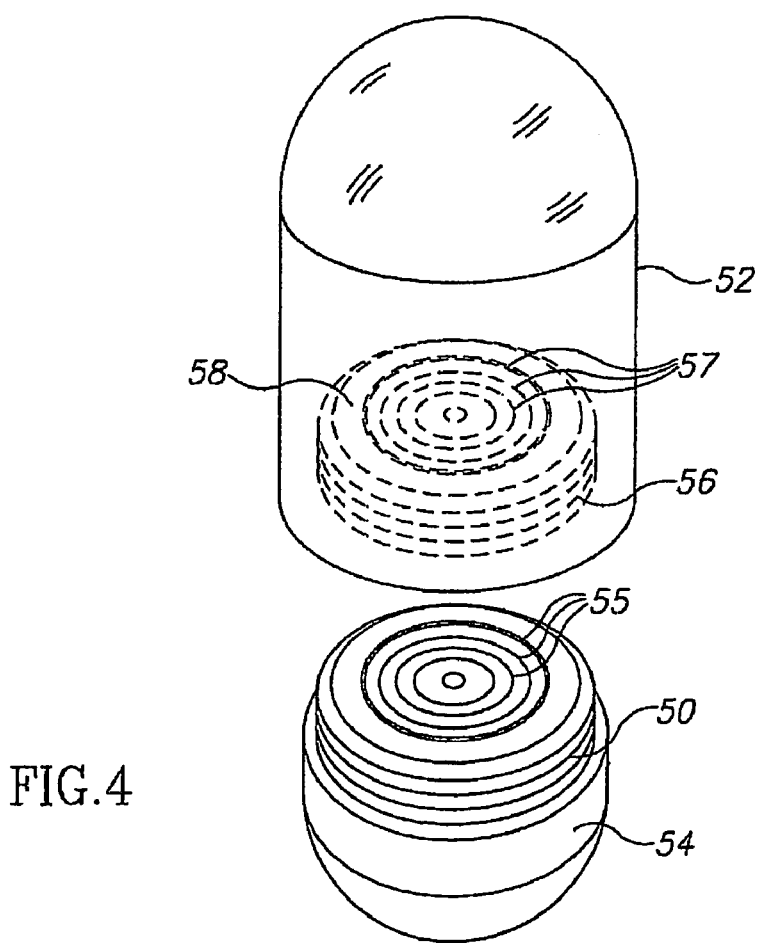
FIGS. 4, 5A, 5B, 6 and 7 are schematic illustrations depicting exemplary attachment systems according to some embodiments of the invention.

According to an embodiment illustrated in FIG. 4, the attachment mechanism may be or may include, for example, a screw mechanism, a threading mechanism or a rotatable mechanism. In FIG. 4, an externally threaded screw 50 is shown on a functional module 54; and a matching, internally threaded portion 56 is shown on a sensing module 52. In alternate embodiments, a reverse arrangement is also possible, e.g., using externally threaded screw 50 on sensing module 52 and internally threaded portion 56 on functional module 54.

In the embodiment shown in FIG. 4, functional module 54 may screw into sensing module 52, e.g., by rotating functional module 54 into sensing module 52. In some embodiments, sensing module 52 may screw into functional module 54; other suitable ways may be used to screw together the functional module 54 and the sensing module 52. In some embodiments, optionally, an adhesive glue may be used to seal the area around screw 50. Other sealants may be used in embodiments of the present invention.

In some embodiments, the attachment mechanism may further incorporate an electrical contact mechanism. For example, FIG. 4 shows metallic rings 55 mounted thereon. Rings 55 may be formed of any suitable electrically conductive metal, for example, copper. Rings 55 may have any suitable shape, for example, they may be circular and concentric, or may include other conducting members or sub-units. Sensing module 52 may have a matching set of metallic rings 57 mounted or formed into a surface 58 at the end of threaded portion 56. When screw 50 is screwed into threaded portion 56, rings 55 may abut or may push up into rings 57, thereby providing electrical contact between modules 52 and 54.

Figure 5A:
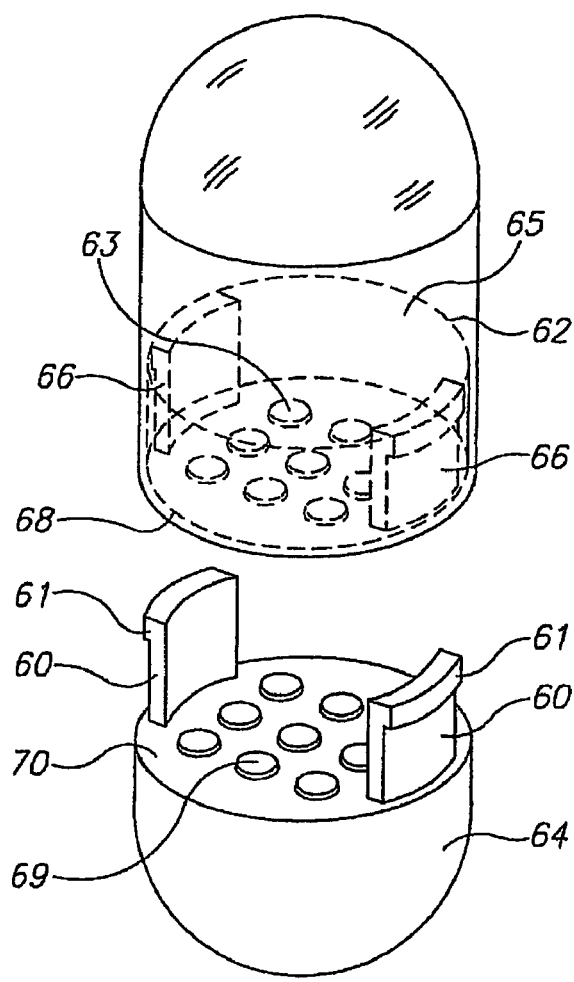

According to some embodiments, as illustrated in FIG. 5A, the attachment mechanism may be or may include, for example, a "snap" mechanism. A functional module 64, may have flexible members 60 with protrusions or projections 61 extending therefrom, e.g., including one or more projections 61 insertable into a fitting or suitable cavity. Projecting from an inside surface 65 of a sensing module may be internal projections 66 or a suitable cavity or chamber. When functional module 64 may be pushed towards imaging module 62, flexible members 60 may enter sensing module 62 until projections 61 may touch internal projections 66. Continued pushing of functional module 64 may cause projections 61 to slide over internal projections 66, thereby "snapping" together or otherwise clinging into place. Internal projections 66 may, for example, prevent functional module 64 from sliding back out. Other suitable protrusions, projections or male-members may be used to allow grasping, holding, attaching or connecting to internal projections, cavities, chambers, or female-members.

In some embodiments, an adhesive glue or other sealant may be used to seal outer surfaces 68 and 70 of modules 62 and 64, respectively, to each other and against the environment. Other sealants may be used. In some embodiments, each of the functional module and the sensing module may be individually sealed, for example, to prevent fluids from entering the modules.

Figure 5B:
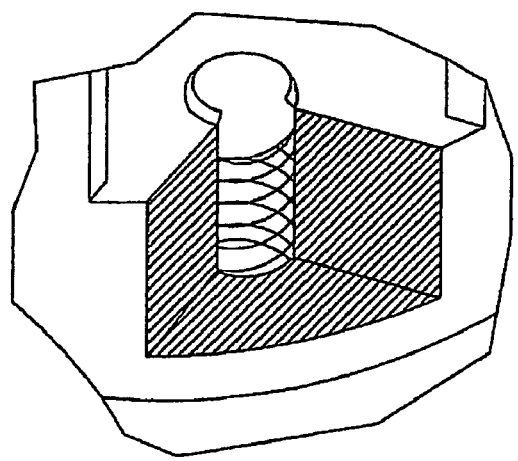

In one embodiment, for example, imaging module 62 may include contacts 63 and functional module 64 may include contacts 69, e.g., ball and spring contacts, as shown in more detail in FIG. 5B.

Figure 6:
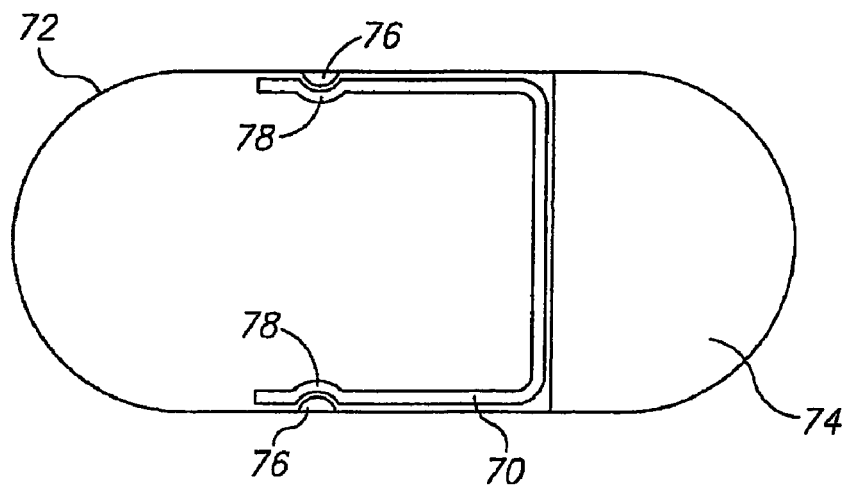

According to some embodiments, as illustrated in FIG. 6, a friction fit sleeve 70 may connect a functional module 74 to a sensing module 72. Friction sleeve 70 may hold and surround a portion of sensing module 72, thereby attaching it to functional module 74.

In one embodiment, other or additional connectors or connection mechanisms may be used, for example, an optional dimple/recess mechanism, in which a first part, e.g., sensing module 72, may include one or more dimples or protrusions 76, and a second part, e.g., friction sleeve 70, may include one or more indentations or recesses 78.

Figure 7:
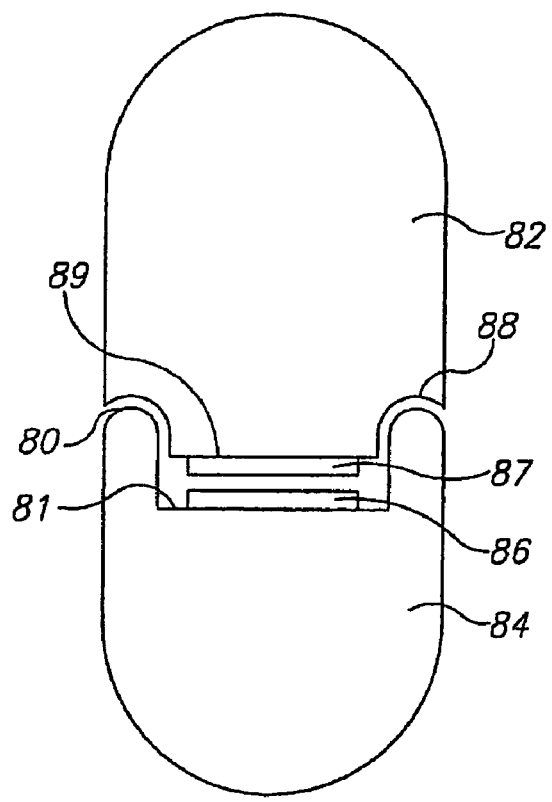

According to some embodiments of the invention, as illustrated in FIG. 7, a functional module 84 may slidingly fit over (or, alternatively, into) a sensing module 82, and may be glued to sensing module 82 using any suitable adhesive or sealant. An external surface 80 of functional module 84 may extend past an inner surface 81 onto which contacts 86 may be mounted. An external surface 88 of sensing module 82 may be indented such that an extension 89 may be formed, on which contacts 87 may be mounted. When functional module 84 is slid onto sensing module 82, contacts 86 may connect to contacts 87. When connected together into a single (e.g., capsule-shaped) in-vivo device, sensing module 82 (e.g., an imaging module 82) and functional module 84 may communicate with each other or may work independently of each other.

Figure 8:
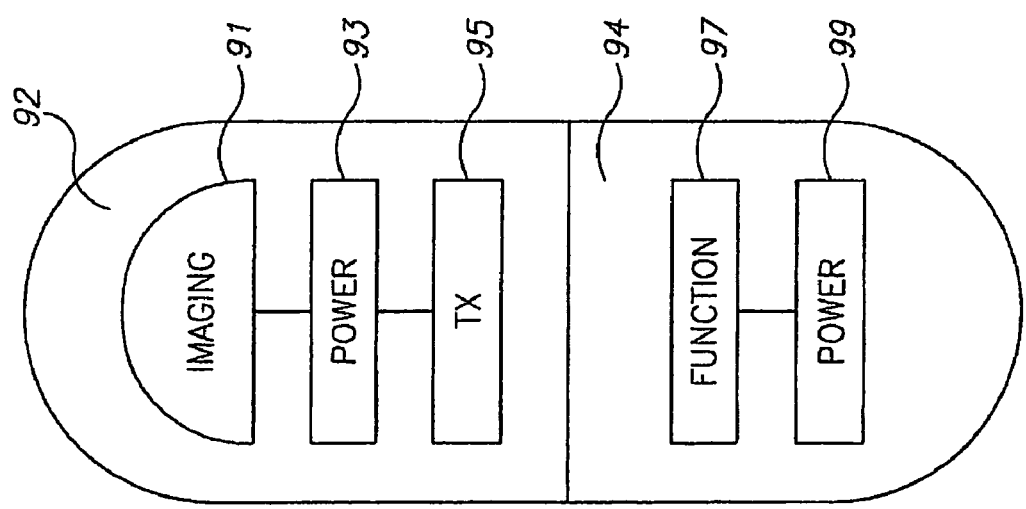

According to some embodiments, as illustrated in FIG. 8, an imaging module 92 may operate independently of a functional module 94. Imaging module 92 may include, for example, an imaging system 91, a power system 93 and a transmitter system 95. Functional module 94 may include, for example, a functional unit 97 and a separate power unit 99. In one embodiment, functional module 94 may provide a function, or several functions, which may operate substantially independently of the imaging and/or transmission operations of imaging module 92. For example, functional unit 97 may include an in-vivo sensor, e.g., a temperature or pH sensor. According to other embodiments, functional unit 97 may include a sample collecting and/or analyzing unit, such as a "lab on a chip". According to some embodiments, functional unit 97 may be or may include a propelling and/or directing device, e.g., for the whole device. Other suitable functions may be provided by functional unit 97 according to various embodiments. Power unit 99 may provide sufficient power to functional unit 94, such that there may be no need for electrical or data communication with imaging module 92.

Figure 9:
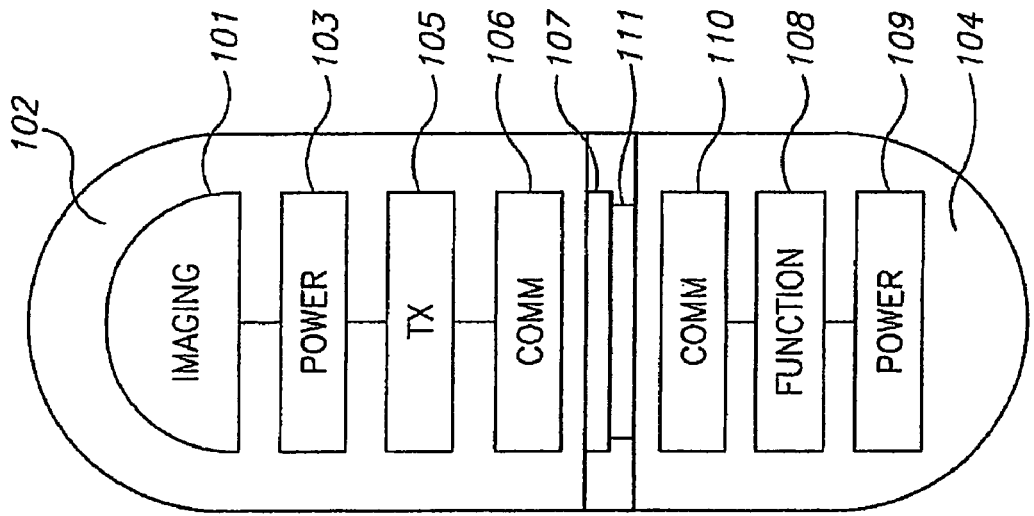
FIGS. 8 and 9 are schematic illustrations of in-vivo sensing devices according to some embodiments of the invention.

According to some embodiments, as illustrated in FIG. 9, an imaging module 102 may include, for example, an imaging system 101, a power system 103, a transmitter system 105, a communication unit 106 and one or more contacts 107. A functional module 104 may include, for example, a functional unit 108, a separate power unit 109, a communication unit 110 and contacts 111. In some embodiments, the functional module 104 may communicate with imaging module 102 and/or may transmit data externally through transmitter system 105. Functional unit 108 may be similar to any of the examples described above, or may have other functionalities. The contacts and connection between the functional module 104 and imaging module 102 may be similar to embodiments described above. According to one embodiment, functional module 104 may act as a power unit for powering imaging module 102, for example, using power unit 109. In one embodiment, it may not be necessary for imaging module 102 to have its own power system 103. In alternate embodiments, power system 103 may be configured for storing energy (e.g., using a chargeable battery or a set of coils for receiving energy from an external source), and may receive energy from power unit 109. In some embodiments, suitable contacts or links, for example, contacts 107, may be used for powering imaging module 102, or induction may be used where no contacts may be necessary between imaging module 102 and functional module 104.

According to some embodiments, the functional module 104 may communicate with imaging module 102 via, for example, a wired communication link, a wireless communication link, Bluetooth communication, RF communication, microwave, or the like. In some embodiments, there may not be any electrical connection and thus, contacts 107 need not be used.

Reference is now made to FIGS. 10-13, which illustrate some exemplary functional modules. For ease of discussion, they are shown with imaging module 82 and with the attachment and electrical contact mechanisms of FIG. 7. It will be appreciated that the functional modules of FIGS. 10-13 may have any other suitable attachment and/or electrical contact mechanisms.

Figure 10:
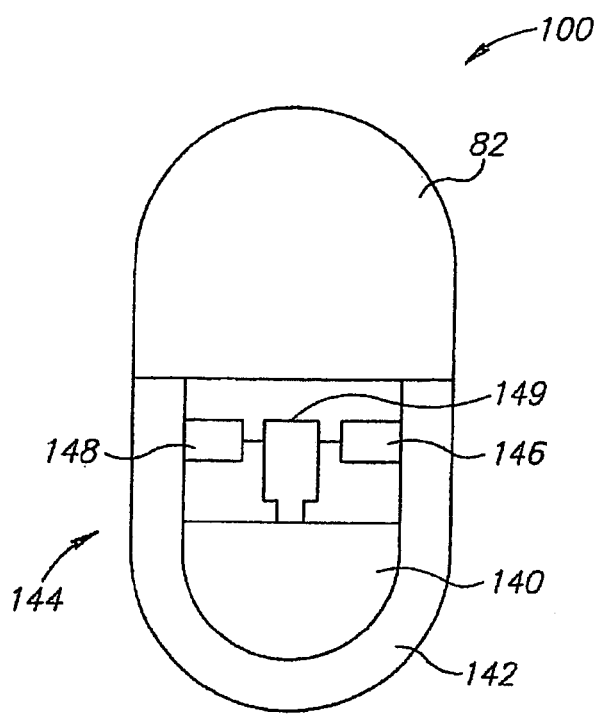
FIG. 10 is a schematic illustration of an in-vivo sensing device configured for changing its geometry, according to one embodiment of the invention.

FIG. 10 shows a functional module 144 according to some embodiments of the invention, which may change its geometry, for example, to brake the motion of the in-vivo device. Module 144 may include, for example, a collapsed balloon 140, a dissolvable shell 142, a power source 146, a control unit 148 and a container 149 of pressurized gas, e.g., air. Dissolvable shell 142 may be formed of any suitable material which may dissolve, e.g., after a pre-defined period of time, or upon reaching a pre-defined body temperature or pH.

Upon dissolving of dissolvable shell 142, a mechanism may be enabled to release pressurized gas from container 149 into collapsed balloon 140, thereby expanding balloon 140. Expanded balloon 140 may change the geometry of the device, for example, expanding the device against the walls of the body lumen, thereby braking the motion of the in-vivo device, stabilizing the device, positioning the in-vivo device in a desired location in a body lumen, etc.

Some embodiments may use other types of modules able to change their geometries, and other suitable methods, for example, a method which need not utilize a dissolvable shell, e.g., as described in embodiments in U.S. patent application Ser. No. 10/423,023, entitled "Device and Method for Orienting a Device In Vivo", filed on Apr. 25, 2003, published on Nov. 20, 2003 as United States Patent Application Publication Number 2003/0216622, assigned to the common assignee of the present application and incorporated herein by reference.

Figures 11, 12:
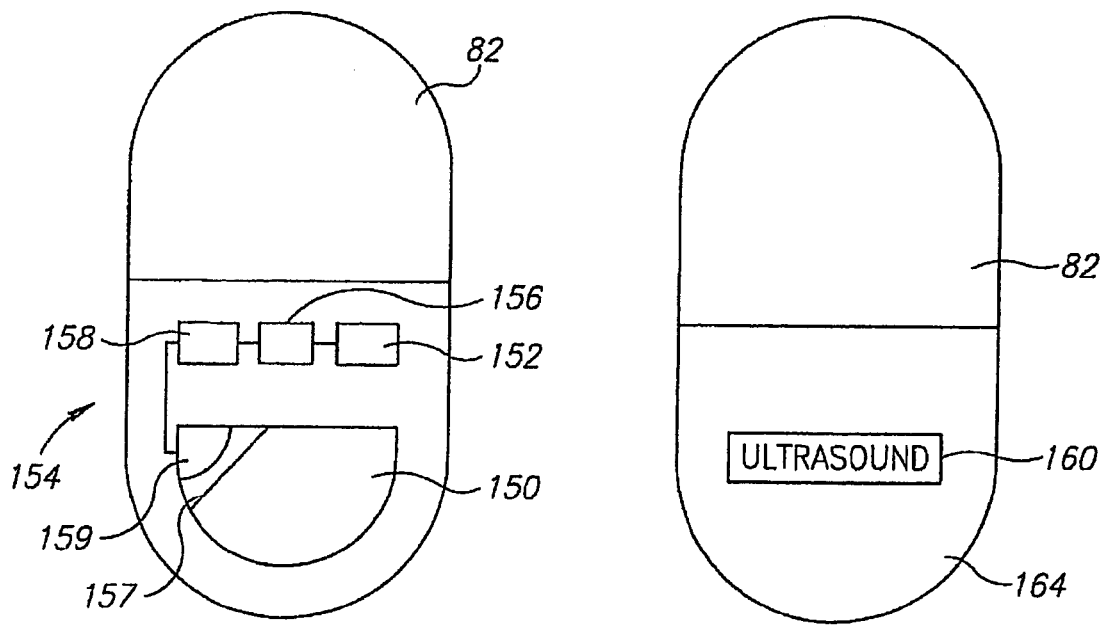
FIG. 11 is a schematic illustration of a sensing device configured for releasing a substance in-vivo, according to one embodiment of the invention.
FIG. 12 is a schematic illustration of a sensing device including ultrasonic imaging capabilities, according to one embodiment of the invention.

FIG. 11 shows a functional module 154 which may serve, for example, as a drug delivery unit. Functional module 154 may include, for example, a drug compartment 150, a control unit 152, a power source 156, a heating element 158, and a flap 159 covering an opening 157 in the outer walls 155 of functional module 154. Drug compartment 150 may store a drug or substance that may be delivered to a desired location in the body. Flap 159 may be formed of a shape memory alloy having a first shape covering opening 157 and a second shape (shown) that may be turned away from opening 157. In some embodiments, for example, the second shape may be present only at a high temperature. When control unit 152 receives a signal to release the drug or substance stored in compartment 150, control unit 152 may activate power source 156 to provide power to heating element 158, thereby heating up heating element 158 to the high temperature at which flap 159 may change to its second shape. When heating element 158 arrives at the desired temperature, flap 159 may change to its second shape, thereby allowing the drug or substance to exit through opening 157.

In an alternate embodiment, drug compartment 150 may be surrounded by a dissolvable shell. The shell may dissolve after a pre-defined time, at a certain temperature or at a pre-determined pH, such that the drug or substance inside compartment 150 may flow out of compartment 150. In this embodiment, them may be no need for control unit 152, power source 156, heating element 158 and/or flap 159.

FIG. 12 shows a functional module 164 having an ultrasound transducer 160 therein. Functional module 164 may be, for example, similar in function to modules described in U.S. patent application Ser. No. 10/365,612, entitled "Device, System and Method for Acoustic In-Vivo Measuring", filed on Feb. 13, 2003, published on Oct. 16, 2003 as United States Patent Application Publication Number 2003/0195415, assigned to the common assignee of the present application and incorporated herein by reference. The device of this embodiment may include, for example, two imagers, e.g., an imager using light in imaging module 82 and an ultrasound imager 160. Functional module 164 may provide an output of ultrasound imager 160 to imaging module 82, e.g., for transmission. The transmission may be substantially in parallel to that of imaging module 82, it may be interleaved with that of imaging module 82, or the imager of imaging module 82 may be used at one point (e.g., in the small intestine) while the ultrasound imager 160 may be utilized at a different point (e.g., in the colon).

Figure 13:
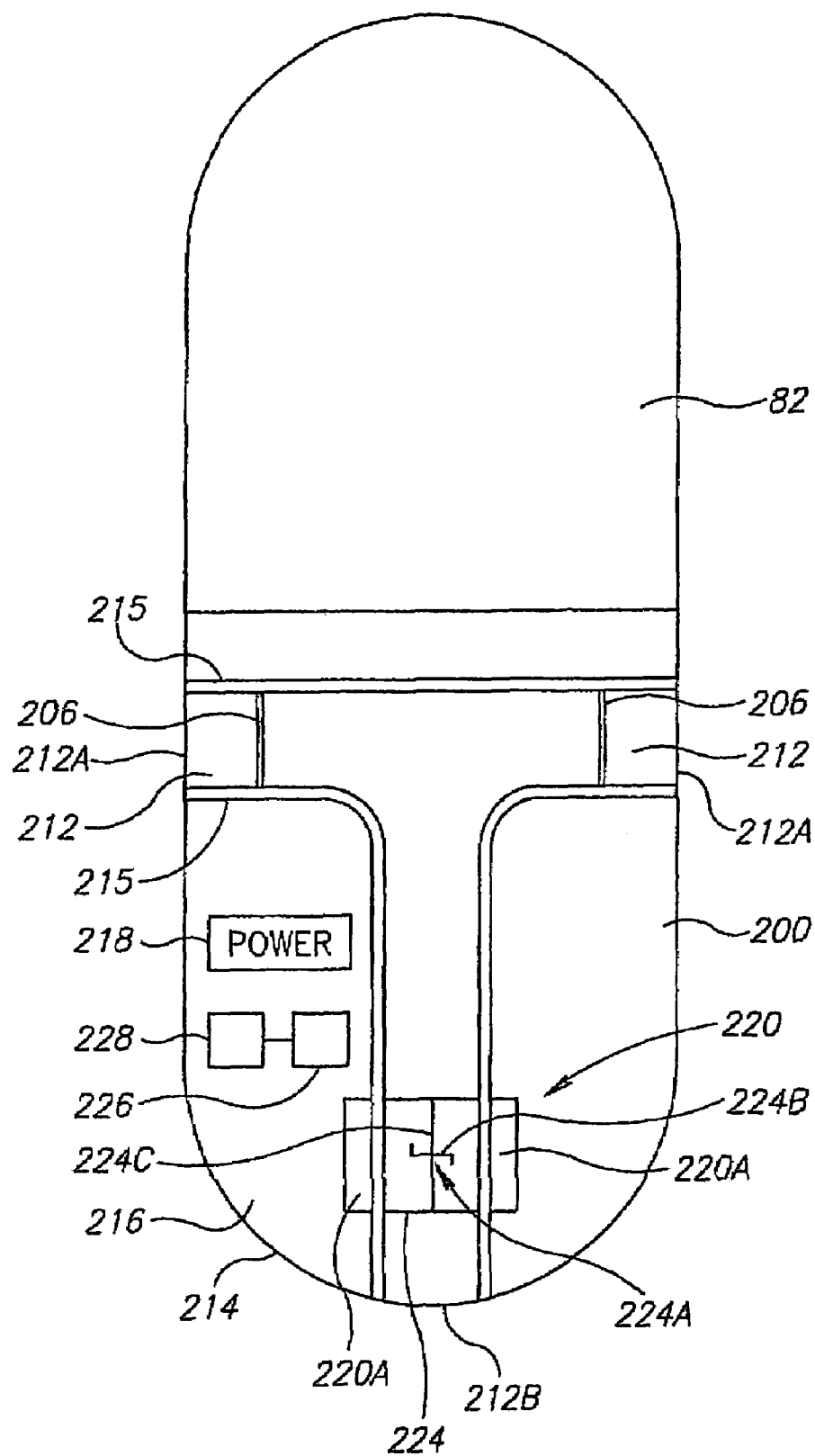
FIG. 13 is a schematic illustration of a sensing device having propulsion, according to one embodiment of the invention.

FIG. 13 shows a functional unit 174, which may provide additional propulsion to the in-vivo device. The functional unit 174 may be similar, for example, to that described in U.S. patent application Ser. No. 10/361,861, entitled "Self Propelled Device Having a Magnetohydrodynamic Propulsion System", filed on Feb. 11, 2003, Published on Nov. 20, 2003 as United States Patent Application Publication Number 2003/0214580, which is assigned to the common assignee of the present invention and is incorporated herein by reference; and/or to that described in U.S. patent application Ser. No. 10/361,855, entitled "Self Propelled Device", filed on Feb. 11, 2003, Published on Nov. 20, 2003 as United States Patent Application Publication Number 2003/0214579, which is assigned to the common assignee of the present invention and is incorporated herein by reference.

In some embodiments, one or more hollow ducts 212 may allow the passage of fluids through the body of a propulsion device 200, and may include one or more inlets 212A and outlets 212B. The one or more ducts 212 may be surrounded, for example, by duct walls 215. Walls 214 of the propulsion device 200 may enclose, for example, one or more volumes 216. The walls 214 of the propulsion device 200 and duct walls 215 may be, for example, the same structures or may be implemented as one unit. Walls 215, walls 214 and/or other structures or components may define the body of device 200.

In some embodiments, propulsion device 200 may include, for example, a motor 220. The motor 220 may include, for example, a stator unit 220A and a rotor unit 224. For example, the rotor unit 224 may be disposed within the duct 212, and the stator unit 220A may be disposed within the volume(s) 216. In some embodiments, the rotor unit 224 may include a propeller unit 224A, including, for example, one or more blades 224B attached to a rotatable axle 224C. The rotatable propeller unit 224A may be, for example, rotatably disposed within a mounting bracket, e.g., similar to that described above.

In some embodiments, propulsion device 200 may further include a power source 218, e.g., suitably connected to motor 220. The power source 218 may include one or more suitable power sources, for example, a battery or power cell. The propulsion device 200 may include, for example, a control unit 228 which may be connected to, or may include, wireless transceiver unit 226, e.g., for external communication.

In some embodiments, during operation, motor 220 may be activated in one or more directions. For example, in one embodiment, motor 220 may be activated in a reverse direction, so that fluid may flow through the ducts 212 in the opposite direction.

While in one embodiment two peripheral inlets 212A are shown, device 200 may include, for example, a ring having any suitable number of inlets or openings. In some embodiments, propeller unit 224A may be positioned other than in the central duct of the ducts 212; for example, one or more propeller units 224A may be placed in any one or more of the peripheral channels of the ducts 212, and more than one propeller unit 224A may be used.

In some embodiments, multiple inlets 212A and/or multiple outlets 212B may be used, and one or more valves, for example, selectively operable valves 206, may be used, e.g., to aid in controlling the direction of movement of propulsion device 200. Valves 206 may be, for example, one-way valves, two-way valves, adjustable valves, or non-adjustable valves; in some embodiments, valves 206 need not be used or included in device 200.

In alternate embodiments, other arrangements of valves, inlets, outlets, ducts, ports, or other suitable components may be used. Further, selective flow control can be provided by, for example, more than one motor or propulsion units, or other suitable components.

Figure 14:
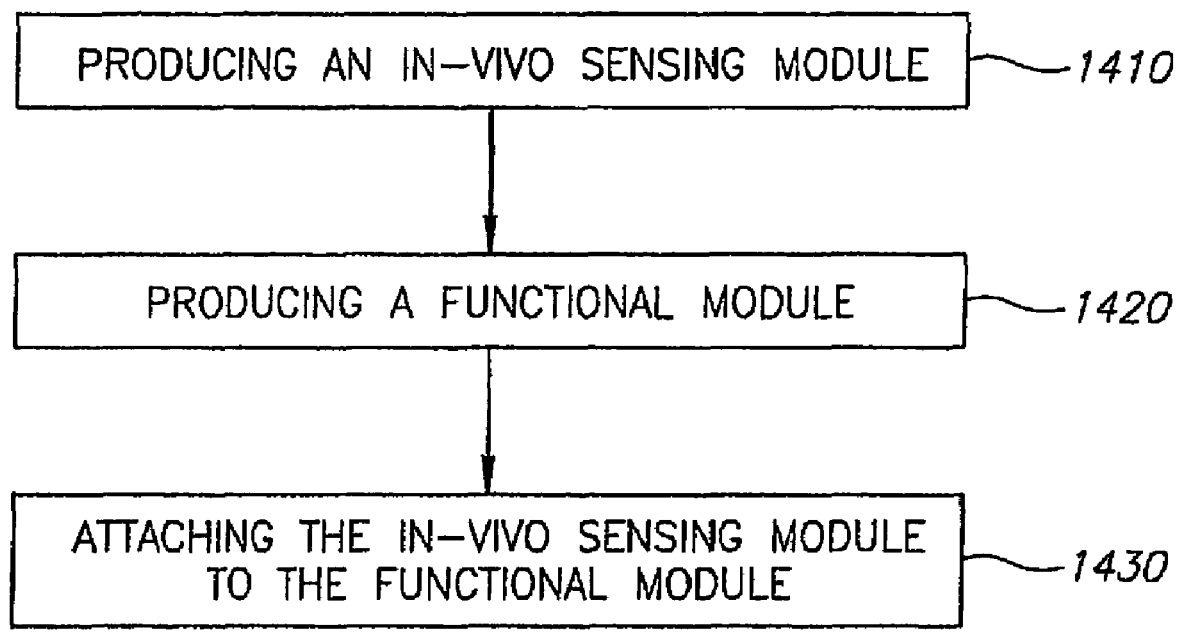
FIG. 14 is a flow-chart of a method of producing an in-vivo sensing device in accordance with some embodiments of the invention.

FIG. 14 is a schematic flow-chart of a method of producing an in-vivo sensing device in accordance with some embodiments of the invention.

As indicated at box 1410, the method may include, for example, producing, manufacturing, or otherwise providing an in-vivo sensing module.

As indicated at box 1420, the method may include, for example, producing, manufacturing, or otherwise providing a functional module.

As indicated at box 1430, the method may include, for example, attaching or connecting the in-vivo sensing module to the functional module, or vice versa, e.g., using an attachment mechanism which may be included in the in-vivo sensing module and/or the functional module. This may be performed, for example, by screwing together the functional module and the in-vivo sensing module, snapping together the functional module and the in-vivo sensing module, gluing together the functional module and the in-vivo sensing module, friction fitting together the functional module and the in-vivo sensing module, connecting a male member and female member attachment mechanism, inserting a male member into a female member, and/or electrically contacting together the functional module and the in-vivo sensing module Other suitable operations or sets of operations may be used in accordance with embodiments of the invention.

It will be appreciated that the functional modules shown and/or described herein are only an exemplary subset of some possible types of functional modules in accordance with embodiments of the invention, and are not limiting in any way. Functional modules according to embodiments of the invention may include various other functions, for example, localization, pressure sensing, additional imagers, various sensors, processing functions, control functions, illumination functions, transmission function, reception functions, power providing functions, image analysis functions, color analysis function, light analysis functions, and/or other suitable functions.

Although part of the discussion herein may relate, for exemplary purposes, to an in-vivo sensing device having one in-vivo sensing module attached to one functional module, or to an in-vivo sensing device having two attached modules, the present invention is not limited in this regard. For example, in accordance with some embodiments, an in-vivo sensing device may include one or more in-vivo sensing modules, which may be attached or detachably attached to one or more functional module, e.g., using one or more attachment mechanisms. For example, in one embodiment, one in-vivo sensing module may be connected to two functional modules, or one functional module may be connected to two in-vivo sensing modules. Other suitable configurations may be used.

In some embodiments, all of the components of the assembled in-vivo imaging or sensing device may be sealed within the device body; the body or shell may include more than one piece. For example, an imager, illumination units, power sources, and transmitting and control units, may all be sealed within the device body or within a housing.

It will be appreciated that the various functional and imaging modules as shown in the drawings have not been drawn to scale. For example, one or more components, modules or functional modules may be larger, smaller, or substantially the same size as, e.g., the imaging module to which it may be attached.

In some embodiments, the in-vivo sensing or imaging device typically may be or may include an autonomous swallowable capsule, but the in-vivo device may have other shapes and need not be swallowable or autonomous. For example, the in-vivo device may be a capsule or other unit where all the components are substantially contained within a container or shell, and where the in vivo device does not require any wires or cables to, for example, receive power or transmit information. In some embodiments, the in-vivo device may communicate with an external receiving and display system to provide display of data, control, or other functions. For example, power may be provided by an internal battery or a wireless receiving system. Other embodiments may have other configurations and capabilities. For example, components may be distributed over multiple sites or units. Control information may be received from an external source.

A system according to some embodiments of the invention may include, for example, an in-vivo sensing or imaging device able to transmit information (e.g., images or other data) to a data receiver and/or recorder, possibly close to or worn on a subject. A data receiver and/or recorder may have other suitable configurations. The data receiver and/or recorder may, for example, transfer the received information to a suitable computing device, e.g., a workstation or a personal computer, where the data may be further analyzed, stored, processed, and/or displayed to a user. In other embodiments, each of the various components need not be required; for example, an internal device may transmit or otherwise transfer information (e.g., using a wire) directly to a viewing or processing system.

Devices, systems and methods in accordance with some embodiments of the invention may be used, for example, in conjunction with an in-vivo device which may be inserted into a human body. However, the scope of the present invention is not limited in this regard; for example, some embodiments of the invention may be used in conjunction with an in-vivo device which may be inserted into a non-human body or an animal body.

Embodiments and/or portions of embodiments discussed herein may be combinable with other embodiments and/or portions of embodiments discussed herein. For example, some aspects or components of the various embodiments discussed herein may be combinable with aspects or components of other embodiments discussed herein.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. An in-vivo imaging device, said imaging device comprising
    an imaging module comprising a housing having a window, said housing enclosing an image sensor, an illumination source, and a transmitter,
    a removable functional module configured to be attached to said imaging module and provide additional electrical power to said imaging module;
    wherein said housing includes an attachment mechanism to attach to, and to provide electrical contact with, the removable functional module,
    wherein the imaging module is configured to operate independently of the removable functional module; and
    wherein, when attached, the imaging module and the removable functional module together form a swallowable in vivo sensing device having a shape of a capsule and retaining said capsule shape at all times while in vivo.

2. The in-vivo imaging device of claim 1, wherein said imaging module is detachably attachable to said removable functional module.

3. The in-vivo imaging device of claim 1, wherein said attachment mechanism comprises a sealant.

4. The in-vivo imaging device of claim 1, wherein said imaging module communicates with said removable functional module through a wireless link.

5. The in vivo sensing device of claim 1, wherein said removable functional module comprises a power source.

6. The in vivo sensing device of claim 1, wherein said imaging module comprises a first in-vivo image sensor and said removable functional module comprises a second image sensor.

7. The in vivo sensing device of claim 1, wherein said removable functional module and said imaging module are sealed to prevent fluids from entering.

8. The in-vivo imaging device of claim 1, wherein said swallowable sensing device is autonomous.

9. The in vivo sensing device of claim 1, wherein one of said imaging module and said removable functional module comprises a male member, and the other of said imaging module and said removable functional module comprises a female member.

10. The in-vivo imaging module device of claim 1, wherein said attachment mechanism comprises a screw mechanism.

11. A swallowable in vivo sensing device comprising an imaging module and a removable functional module configured to be attached to one another,
    said imaging module comprising
        a housing having a window, said housing enclosing an image sensor, an illumination source, and a transmitter, wherein said housing includes an attachment mechanism to attach to, and to provide electrical contact with, the removable functional module,
        wherein the imaging module is configured to operate independently of the removable functional module, and
    said removable functional module providing additional electrical power to said imaging module; and
    wherein, when attached, the imaging module and the removable functional module together form a swallowable in vivo sensing device having a shape of a capsule and retaining said capsule shape at all times while in vivo.

12. The in-vivo sensing device of claim 11, wherein said imaging module is detachably attachable to said removable functional module.

13. The in-vivo sensing device of claim 11, wherein said attachment mechanism comprises a sealant.

14. The in-vivo sensing device of claim 11, wherein said imaging module communicates with said removable functional module through a wireless link.

15. The in-vivo sensing device of claim 11, wherein said removable functional module comprises a non-imaging sensor.

16. The in-vivo sensing device of claim 11, wherein said imaging module comprises a first in-vivo imager and said removable functional module comprises a second in-vivo imager.

17. The in-vivo sensing device of claim 11, wherein each of said removable functional module and said imaging module is sealed to prevent fluids from entering.

18. The in-vivo sensing device of claim 11, wherein said swallowable sensing device is autonomous.

19. The in-vivo sensing device of claim 11, wherein one of said imaging module and said removable functional module comprises a male member, and the other of said imaging module and said removable functional module comprises a female member.

20. The in vivo sensing device of claim 11, wherein said attachment mechanism comprises a screw mechanism.

* * * * *

UNITED STATES PATENT AND TRADEMARK OFFICE
CERTIFICATE OF CORRECTION

PATENT NO. : 7,647,090 B1
APPLICATION NO. : 11/024906
DATED : January 12, 2010
INVENTOR(S) : Frisch et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 718 days.

Signed and Sealed this

Twenty-eighth Day of December, 2010

David J. Kappos
*Director of the United States Patent and Trademark Office*